United States Patent
Iaccino et al.

(10) Patent No.: US 7,772,450 B2
(45) Date of Patent: Aug. 10, 2010

(54) PRODUCTION OF AROMATIC HYDROCARBONS AND SYNGAS FROM METHANE

(75) Inventors: Larry L. Iaccino, Seabrook, TX (US); James R. Lattner, LaPorte, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 775 days.

(21) Appl. No.: 11/789,875

(22) Filed: Apr. 26, 2007

(65) Prior Publication Data

US 2008/0021251 A1   Jan. 24, 2008

Related U.S. Application Data

(60) Provisional application No. 60/816,097, filed on Jun. 23, 2006.

(51) Int. Cl.
*C07C 2/78* (2006.01)
(52) U.S. Cl. .................. 585/943; 585/324; 585/357; 585/365; 585/379; 585/407; 585/540
(58) Field of Classification Search .................. 585/943
See application file for complete search history.

(56) References Cited

U.S. PATENT DOCUMENTS

| | | | |
|---|---|---|---|
| 2,135,441 A | | 11/1938 | Schauer |
| 2,360,463 A | * | 10/1944 | Arveson ...................... 208/64 |
| 4,727,206 A | | 2/1988 | Clayson et al. |
| 4,806,699 A | | 2/1989 | Smith et al. |
| 5,026,937 A | | 6/1991 | Bricker |
| 5,336,825 A | | 8/1994 | Choudhary et al. |
| 5,936,135 A | | 8/1999 | Choudhary et al. |
| 6,239,057 B1 | | 5/2001 | Ichikawa et al. |
| 6,426,442 B1 | | 7/2002 | Ichikawa et al. |
| 6,552,243 B2 | | 4/2003 | Allison et al. |
| 7,019,184 B2 | * | 3/2006 | Allison et al. ............... 585/415 |
| 7,208,647 B2 | * | 4/2007 | Peterson et al. ............. 585/324 |
| 2004/0192990 A1 | * | 9/2004 | Choudhary et al. ......... 585/638 |
| 2004/0267079 A1 | * | 12/2004 | Mamedov et al. ........... 585/943 |

FOREIGN PATENT DOCUMENTS

| | | |
|---|---|---|
| EP | 0 269 297 | 6/1988 |
| WO | WO 2006/087971 A1 * | 8/2006 |

OTHER PUBLICATIONS

Japan Chemical Week Incorporating Asia Report, "Benzene Synthesized Directly from Methane: Mitsubishi Chem", The Chemical Daily Co., Ltd., vol. 46, No. 2337, ISSN 0047-1755, Oct. 6, 2005.

* cited by examiner

*Primary Examiner*—Tam M Nguyen
(74) *Attorney, Agent, or Firm*—Andrew B. Griffis

(57) ABSTRACT

In a process for converting methane to syngas and aromatic hydrocarbons, a feed containing methane is contacted with a dehydrocyclization catalyst under conditions effective to convert said methane to aromatic hydrocarbons and produce a first effluent comprising aromatic hydrocarbons and $H_2$, wherein said first effluent comprises at least 5 wt % more aromatic hydrocarbons than said feed. At least part of the $H_2$ from said first effluent is then reacted with an oxygen-containing species, such as carbon dioxide, to produce a second effluent having an increased $H_2$ and CO content compared with said first effluent.

50 Claims, No Drawings

PRODUCTION OF AROMATIC HYDROCARBONS AND SYNGAS FROM METHANE

PRIORITY CLAIM

This application claims the benefit of U.S. Provisional application No. 60/816,097, filed Jun. 23, 2006, the entirety of which is incorporated by reference.

FIELD

This disclosure relates to a process for producing aromatic hydrocarbons and syngas from methane.

BACKGROUND

Aromatic hydrocarbons, particularly benzene, toluene, ethylbenzene, and xylenes, are important commodity chemicals in the petrochemical industry. Currently, aromatics are most frequently produced from petroleum-based feedstocks by a variety of processes, including catalytic reforming and catalytic cracking. However, as world supplies of petroleum feedstocks decrease, a growing need to find alternative sources of aromatic hydrocarbons exists.

One possible alternative source of aromatic hydrocarbons is methane, which is the major constituent of natural gas and biogas. Because of the problems associated with transportation of large volumes of natural gas, most of the natural gas produced along with oil, particularly at remote places, is flared. Hence the conversion of alkanes contained in natural gas directly to higher hydrocarbons, such as aromatics, is a particularly attractive method of upgrading natural gas, providing that the attendant technical difficulties can be overcome.

A majority of the processes for converting methane to liquid hydrocarbons first involve conversion of the methane to syngas, a blend of hydrogen ($H_2$) and carbon oxides (CO and/or $CO_2$). Production of syngas can be capital and energy intensive. However, aromatics generation processes that can co-produce syngas are particularly valuable as syngas can have high value disposition. Syngas has high potential value because it may be further reacted to form methanol, higher alcohols, acetic acid, ammonia, acetone, acetaldehyde, ethylene oxide, ethylene glycol, dimethyl ether, gasoline, or Fischer Tropsch Liquids ("FTL"). Generation of such a diverse yield slate is preferable as these chemicals have a higher value than methane and are easier to transport for sale.

A number of alternative processes have been proposed for converting methane to higher hydrocarbons. One such process involves catalytic oxidative coupling of methane to olefins followed by the catalytic conversion of the olefins to liquid hydrocarbons, including aromatic hydrocarbons. For example, U.S. Pat. No. 5,336,825 discloses a two-step process for the oxidative conversion of methane to gasoline range hydrocarbons comprising aromatic hydrocarbons. In the first step, methane is converted to ethylene and minor amounts of $C_3$ and $C_4$ olefins in the presence of free oxygen using a rare earth metal promoted alkaline earth metal oxide catalyst at a temperature between 500° C. and 1000° C. The ethylene and higher olefins formed in the first step are then converted to gasoline range liquid hydrocarbons over an acidic solid catalyst containing a high silica pentasil zeolite.

Dehydroaromatization of methane via high-temperature reductive coupling has also been proposed as a route for upgrading methane into higher hydrocarbons, particularly ethylene, benzene, and naphthalene. For example, U.S. Pat. No. 4,727,206 discloses a process for producing liquids rich in aromatic hydrocarbons by contacting methane at a temperature between 600° C. and 800° C. in the absence of oxygen with a catalyst composition comprising an aluminosilicate having a silica to alumina molar ratio of at least 5:1, said aluminosilicate being loaded with (i) gallium or a compound thereof and (ii) a metal or a compound thereof from Group 7 of the Periodic Table.

U.S. Pat. No. 5,026,937 discloses a process for the aromatization of methane which comprises the steps of passing a feed stream, which comprises over 0.5 mole percent ("mole %") hydrogen and 50 mole % methane, into a reaction zone having at least one bed of solid catalyst comprising ZSM-5 and phosphorous-containing alumina at conversion conditions which include a temperature of 550° C. to 750° C., a pressure less than 1000 kpaa (pressure absolute) and a gas hourly space velocity of 400 to 7,500 $hr^{-1}$. The product effluent is said to include methane, hydrogen, at least 3 mole % $C_2$ hydrocarbons and at least 5 mole % $C_6$-$C_8$ aromatic hydrocarbons. After condensation to remove the $C_4$-plus hydrocarbon fraction, cryogenic techniques are proposed to separate the hydrogen and light hydrocarbons (e.g., methane, ethane, ethylene, etc.) in the product effluent.

U.S. Pat. No. 5,936,135 discloses a low temperature, non-oxidative process for the conversion of a lower alkane, such as methane or ethane, to aromatic hydrocarbons. In this process, the lower alkane is mixed with a higher olefin or paraffin, such as propylene or butene, and the mixture is contacted with a pretreated bifunctional pentasil zeolite catalyst, such as GaZSM-5, at a temperature of 300° C. to 600° C., a gas hourly space velocity of 1000 to 100,000 $cm^3 g^{-1} hr^{-1}$ and a pressure of 100 to 500 kPa. Pretreatment of the catalyst involves contacting the catalyst with a mixture of hydrogen and steam at a temperature of 400° C. to 800° C., a pressure of 100 to 500 kPa and a gas hourly space velocity of at least 500 $cm^3 g^{-1} hr^{-1}$ for a period of at least 0.5 hour and then contacting the catalyst with air or oxygen at a temperature of 400° C. to 800° C., a gas hourly space velocity of at least 200 $cm^3 g^{-1} hr^{-1}$ and a pressure of 100 to 500 kPa for a period of at least 0.2 hour.

U.S. Pat. Nos. 6,239,057 and 6,426,442 disclose a process for producing higher carbon number hydrocarbons, e.g., benzene, from low carbon number hydrocarbons, such as methane, by contacting the latter with a catalyst comprising a porous support, such as ZSM-5, which has dispersed thereon rhenium and a promoter metal such as iron, cobalt, vanadium, manganese, molybdenum, tungsten or a mixture thereof. The addition of CO or carbon dioxide ($CO_2$) to the feed is said to increase the yield of benzene and the stability of the catalyst.

U.S. Pat. No. 6,552,243 discloses a process for the non-oxidative aromatization of methane, in which a catalyst composition comprising a metal-loaded, crystalline aluminosilicate molecular sieve is initially activated by treatment with a mixture of hydrogen and a $C_2$ to $C_4$ alkane, preferably butane, and then the activated catalyst is contacted with a feed stream comprising at least 40 mole % methane at a temperature of 600° C. to 800° C., a pressure of less than 500 kPaa, and a weight hourly space velocity ("WHSV") of 0.1 to 10 $hr^{-1}$.

Russian Patent No. 2,135,441 discloses a process for converting methane to heavier hydrocarbons, in which the methane is mixed with at least 5 wt % of a $C_3$-plus hydrocarbon, such as benzene, and then contacted in a multi-stage reactor system with a catalyst comprising metallic platinum having a degree of oxidation greater than zero at a methane partial pressure of at least 0.05 MPa and a temperature of at least 440° C. Hydrogen generated in the process may be contacted with oxides of carbon to generate additional methane that, after removal of the co-produced water, can be added to the methane feed. The products of the methane conversion are a $C_2$-$C_4$ gaseous phase and a $C_5$-plus hydrocarbon liquid phase but, according the Examples, there is little (less than 5 wt %) or no net increase in aromatic rings as compared with the feed.

Existing proposals for the conversion of methane to aromatic hydrocarbons suffer from a variety of problems that have limited their commercial potential. Oxidative coupling methods generally involve highly exothermic and potentially hazardous methane combustion reactions, frequently require expensive oxygen generation facilities. Additionally, existing reductive coupling techniques frequently have low selectivity to aromatics and may require expensive co-feeds to improve conversion and/or aromatics selectivity. Moreover, any reductive coupling process generates large quantities of hydrogen and thus requires, for economic viability, a route for effective utilization of the hydrogen by-product. Since natural gas fields are frequently at remote locations, effective hydrogen utilization can present a substantial challenge.

A particular difficulty in using natural gas as an aromatics source concerns the fact that many natural gas fields around the world contain large quantities, sometimes in excess of 50 volume %, of carbon dioxide. Any process that requires separation and disposal of large quantities of carbon dioxide from natural gas is likely to be economically prohibitive. In fact, some natural gas fields have such high levels of carbon dioxide as to be currently considered economically unrecoverable.

While there are numerous published processes for producing syngas from $CO_2$ containing natural gas—commonly referred to as dry reforming—these are limited to producing 1:1$H_2$:CO due to the stoichiometry of the reaction: $CO_2 + CH_4 \leftrightarrow 2CO + 2H_2$. Typically, syngas with higher ratio of $H_2$:CO is desired. For example, for methanol synthesis a ratio of about 2.08$H_2$:CO syngas is desired, while for FTL a ratio of about 1.5 to 2.5$H_2$:CO syngas is desired. By co-feeding steam with the $CO_2$ and methane, higher ratio syngas can be produced, but the $CO_2$ content of the feed stream is now limited so that higher $CO_2$ containing gas fields can not be utilized. For example, to produce 2.0$H_2$:CO syngas, one would be limited to a maximum $CO_2$ content in the natural gas of 25 volume %; based on the stoichiometry of the reaction: $3CH_4 + CO_2 + 2H_2O \leftrightarrow 8H_2 + 4CO$.

Therefore, there is a need for an improved process for converting methane to aromatic hydrocarbons, particularly when the methane is present in a natural gas stream containing large quantities of carbon dioxide. Co-production of a desirable range $H_2$:CO syngas can further improve the attractiveness of the process.

U.S. Pat. No. 4,806,699 discloses a process for the production of aromatic hydrocarbons from a feedstock comprising ethane and/or propane and/or butane which process comprises the steps of: (A) reacting the feedstock in the presence of a dehydrocyclodimerisation catalyst to produce a product comprising aromatic hydrocarbons, hydrogen and methane, (B) separating the product of step (A) into an aromatic hydrocarbon fraction, a methane-rich gaseous fraction and a hydrogen-rich gaseous fraction, (C) feeding all or part of the methane-rich gaseous fraction separated in step (B) to a synthesis gas production unit, thereby to produce synthesis gas comprising hydrogen and carbon monoxide in a ratio less than or equal to 2:1, and (D) contacting the synthesis gas from step (C) together with all or part of the hydrogen-rich gaseous fraction separated in step (B), thereby increasing the hydrogen to carbon monoxide ratio of the synthesis gas to a value greater than 2:1, with a Fischer-Tropsch conversion catalyst to produce a hydrocarbon product.

SUMMARY

In one embodiment, this disclosure relates to a process for converting a feed containing methane to syngas and higher hydrocarbons including aromatic hydrocarbons, the process comprising:
(a) contacting a feed containing methane with a dehydrocyclization catalyst under conditions effective to produce a first effluent comprising said aromatic hydrocarbons, residual methane, and $H_2$, wherein said first effluent has a concentration of aromatic rings which is at least 5 wt % greater than the concentration of aromatic rings in said feed;
(b) recovering at least a portion of said aromatic hydrocarbons from said first effluent; and
(c) reacting at least part of said $H_2$ and said residual methane from said first effluent with an oxygen-containing species to produce a second effluent having $H_2$ and CO, wherein the total number of moles of $H_2$ and CO in said second effluent is greater than the total number of moles of $H_2$ and CO in said first effluent.

Conveniently, said feed in said step (a) further comprises at least one of $H_2$, water ($H_2O$), $O_2$, CO, and $CO_2$.

Conveniently, said feed in said step (a) comprises less than 5 wt % of $C_3+$ hydrocarbons. As used herein, the term "$C_3+$ hydrocarbons" means hydrocarbons having 3 or more carbon atoms.

Conveniently, said conditions in said step (a) are non-oxidizing conditions. By "non-oxidizing" it is meant that oxidizing agents (such as, $O_2$, $NO_x$, and metal oxides which can release oxygen to oxidize methane to $CO_x$) are present at less than 5%, preferably at less then 1%, and most preferably at less than 0.1%, of the amount required for stoichiometric oxidation of all the methane in the feed.

Typically said conditions in said step (a) include a temperature of from about 400° C. to about 1200° C., or preferably of from about 500° C. to about 975° C., or more preferably of from about 600° C. to about 950° C.

Conveniently, said oxygen-containing species in said step (b) comprises an oxide of carbon, such as carbon dioxide, for example, carbon dioxide from a natural gas stream which may also contain at least part of the methane in the feed in said step (a). Alternatively, said oxygen-containing species in said step (b) comprises molecular oxygen, such as $O_2$. In another embodiment, said oxygen-containing species in said step (b) comprises water. Depending on the downstream utilization of the syngas, the oxygen species may be varied combinations of $CO_2$, $H_2O$ and $O_2$ to obtain the desired $H_2$ to CO ratio needed by the given downstream process.

Typically, the aromatic hydrocarbons recovered in (b) comprise benzene and/or naphthalene. In one embodiment, such recovery of the aromatic hydrocarbon is carried out prior to (c).

Conveniently, before or after said recovering, at least a portion of the aromatic compounds in said first effluent can be alkylated with an alkylating agent. In one embodiment, the alkylating agent is ethylene produced in said contacting (a). In another embodiment, the alkylating agent comprises carbon monoxide and $H_2$ or a reaction product thereof, wherein a portion of the carbon monoxide may be produced in step (c).

In one embodiment, at least part of the benzene and/or naphthalene recovered from the first effluent steam is reacted with $H_2$ from the first effluent to produce one or more of cyclohexane, dihydronaphthalene (benzylcyclohexene), tetrahydronaphthalene (tetralin), hexahydronaphthalene (dicyclohexene), octahydronaphthalene, and decahydronaphthalene (decalin).

In a further embodiment, the present disclosure relates to a process for converting a feed containing methane to syngas and higher hydrocarbons including aromatic hydrocarbons, the process comprising:
(a) contacting a feed containing methane with a dehydrocyclization catalyst under conditions effective to produce a first effluent comprising said aromatic hydrocarbons, residual methane, and $H_2$, wherein said first effluent has a concentration of aromatic rings which is at least 5 wt % greater than the concentration of aromatic rings in said feed;
(b) recovering at least a portion of said aromatic hydrocarbons from said first effluent; and
(c) reacting at least part of said $H_2$ and said residual methane from said first effluent with $CO_2$, $H_2O$, and/or $O_2$ to produce a second effluent comprising $H_2$, CO, and methane, wherein the total number of moles of $H_2$ and CO in said second effluent is greater than the total number of moles of $H_2$ and CO in said first effluent.

Conveniently, the process further includes recovering at least part of said residual methane in said first effluent and recycling it to said contacting (a). In one embodiment, recovering said methane is accomplished by separation of a portion of the methane from the first effluent prior to said reacting (c). Conveniently, said separation is carried out by one or more of adsorption, absorption, membrane permeation, and cryogenic distillation.

Conveniently, the process further includes recovering at least part of said methane in said second effluent and recycling it to said contacting (a).

If said separation results in residual $H_2$ in the methane stream for recycle, a $H_2$ rejection step may be employed to reduce the quantity of said $H_2$ in the recovered methane.

It is to be appreciated that references herein to the first effluent comprising at least 5 wt % more aromatic rings than the feed is intended to mean that the total number of aromatic rings in the first effluent should exceed the total number of aromatic rings in the feed by at least 5 wt %. For example, if the feed contains 1 wt % of aromatic rings, the first effluent will contain at least 6 wt % of aromatic rings. Changes in substituents on any aromatic rings between the feed and the first effluent are not included in this calculation.

It is also to be appreciated that references herein to the second effluent containing more $H_2$ and CO than said first effluent is meant to mean that the total number of moles of $H_2$ and moles of CO is increased; in some cases the moles of $H_2$ will be reduced but the total number of moles of $H_2$ and CO will always be increased.

DETAILED DESCRIPTION OF THE EMBODIMENTS

The present disclosure provides a process for converting a feed containing methane to aromatic hydrocarbon(s) and syngas by subjecting said feed, typically together with CO and/or $CO_2$, to a dehydrocyclization step under conditions effective to produce a first effluent comprising said aromatic hydrocarbons, residual methane, and $H_2$, wherein said first effluent comprises at least 5 wt % more aromatic rings than said feed. The first effluent is then subjected to a syngas generation step in which at least part of said $H_2$ and the residual methane from said first effluent is reacted with an oxygen-containing species to produce a second effluent having a increased $H_2$ and CO content as compared with said first effluent. At least a portion of the aromatic hydrocarbon(s), such as benzene, is recovered from said first effluent although, if desired, the aromatic hydrocarbon(s) can be subjected to an alkylation step prior to or after recovery from the first effluent. In addition, the process normally includes additional steps, referred to herein as hydrogen rejection, to convert additional $H_2$ in the first effluent to higher value products.

Feedstock

Any methane-containing feedstock can be used in the present process but, in general, the present process is intended for use with a natural gas feedstock. Other suitable methane-containing feedstocks include those obtained from sources such as coal beds, landfills, agricultural or municipal waste fermentation, or refinery gas streams.

Methane-containing feedstocks, such as natural gas, typically contain carbon dioxide and ethane in addition to methane. Ethane and other aliphatic hydrocarbons that may be present in the feed can, of course, be converted to desired aromatics products in the dehydrocyclization step. In addition, as will be discussed below, carbon dioxide can also be converted to useful syngas.

Nitrogen and sulfur impurities are also typically present in methane-containing streams and may be removed or reduced to low levels, prior to use of the streams in the process of the disclosure. In an embodiment, the feed to the dehydrocyclization step contains less than 100 ppm, or less than 10 ppm, or less than 1 ppm of each nitrogen and sulfur compounds.

In addition to methane, the feed to the dehydrocyclization step may comprise at least one of $H_2$, water, $O_2$, carbon monoxide, or carbon dioxide, in order to assist in coke mitigation. These additives can be introduced as separate co-feeds or can be present in the methane stream, such as, for example, when the methane stream is derived from natural gas containing carbon dioxide. Other sources of carbon dioxide may include flue gases, liquefied natural gas ("LNG") plants, hydrogen plants, ammonia plants, glycol plants, and phthalic anhydride plants.

In one embodiment, the feed to the dehydrocyclization step comprises 90 to 99.9 mol %, such as 97 to 99 mol %, methane and 0.1 to 10 mol %, such as 1 to 3 mol %, $CO_2$. In another embodiment, the feed to the dehydrocyclization step comprises 80 to 99.9 mol %, such as 94 to 99 mol %, methane and 0.1 to 20 mol %, such as 1 to 6 mol %, CO. In a further embodiment, the feed to the dehydrocyclization step comprises 90 to 99.9 mol %, such as 97 to 99 mol %, methane and 0.1 to 10 mol %, such as 1 to 5 mol %, steam. In yet a further embodiment, the feed to the dehydrocyclization step comprises 80 to 99.9 mol %, such as 95 to 99 mol %, methane and 0.1 to 20 mol %, such as 1 to 5 mol %, $H_2$.

The feed to the dehydrocyclization step can also contain higher hydrocarbons than methane, including aromatic hydrocarbons. Such higher hydrocarbons can be recycled from downstream processes, added as separate co-feeds or can be present in the methane stream, such as, for example, when ethane is present in a natural gas feed. Higher hydrocarbons recycled from the downstream processes typically include one-ring aromatics and/or paraffins and olefins having predominately 6 or less, such as 5 or less, for example 4 or less, typically 3 or less carbon atoms. In general, the feed to the dehydrocyclization step contains less than 5 wt %, such as less than 3 wt %, of $C_3$+ hydrocarbons.

Dehydrocyclization

In the dehydrocyclization step of the present process, the feed containing methane is contacted with a dehydrocyclization catalyst under conditions, normally non-oxidizing conditions and preferably reducing conditions, effective to convert the methane to higher hydrocarbons, including benzene and naphthalene. The principal net reactions involved are as follows:

$$2CH_4 \leftrightarrow C_2H_4 + 2H_2 \quad \text{(Reaction 1)}$$

$$6CH_4 \leftrightarrow C_6H_6 + 9H_2 \quad \text{(Reaction 2)}$$

$$10CH_4 \leftrightarrow C_{10}H_8 + 16H_2 \quad \text{(Reaction 3)}$$

Carbon monoxide and/or dioxide that may be present in the feed improves catalyst activity and stability by facilitating reactions such as:

$$CO_2 + coke \rightarrow 2CO \quad \text{(Reaction 4)}$$

but negatively impacts equilibrium by allowing competing net reactions, such as;

$$CO_2 + CH_4 \leftrightarrow 2CO + 2H_2 \quad \text{(Reaction 5)}$$

Any dehydrocyclization catalyst effective to convert methane to aromatics can be used in the present process, although generally the catalyst will include a metal component, particularly a transition metal or compound thereof, on an inorganic support. Preferably, the metal component is present in an amount between 0.1% and 20%, or between 1% and 10%, by weight of the total catalyst.

Suitable metal components for the catalyst include calcium, magnesium, barium, yttrium, lanthanum, scandium, cerium, titanium, zirconium, hafnium, vanadium, niobium, tantalum, chromium, molybdenum, tungsten, manganese, rhenium, iron, ruthenium, cobalt, rhodium, iridium, nickel, palladium, copper, silver, gold, zinc, aluminum, gallium, silicon, germanium, indium, tin, lead, bismuth, and transuranium metals. Such metal components may be present in elemental form or as metal compounds, such as oxides, carbides, nitrides, and/or phosphides, and may be employed alone or in combination. Platinum and osmium can also be used as one of the metal component but, in general, are not preferred.

The inorganic support may be either amorphous or crystalline and in particular may be an oxide, carbide or nitride of boron, aluminum, silicon, phosphorous, titanium, scandium, chromium, vanadium, magnesium, manganese, iron, zinc, gallium, germanium, yttrium, zirconium, niobium, molybdenum, indium, tin, barium, lanthanum, hafnium, cerium, tantalum, tungsten, or other transuranium elements. In addition, the support may be a porous material, such as a microporous crystalline material or a mesoporous material. As used herein the term "microporous" refers to pores having a diameter of less than 2 nanometers, whereas the term "mesoporous" refers to pores having a diameter of from 2 to 50 nanometers.

Suitable microporous crystalline materials include silicates, aluminosilicates, titanosilicates, aluminophosphates, metallophosphates, silicoaluminophosphates, or their mixtures. Such microporous crystalline materials include materials having the framework types MFI (e.g., ZSM-5 and silicalite), MEL (e.g., ZSM-11), MTW (e.g., ZSM-12), TON (e.g., ZSM-22), MTT (e.g., ZSM-23), FER (e.g., ZSM-35), MFS (e.g., ZSM-57), MWW (e.g., MCM-22, PSH-3, SSZ-25, ERB-1, ITQ-1, ITQ-2, MCM-36, MCM-49, and MCM-56), IWR (e.g., ITQ-24), KFI (e.g., ZK-5), BEA (e.g., zeolite beta), ITH (e.g., ITQ-13), MOR (e.g., mordenite), FAU (e.g., zeolites X, Y, ultrastabilized Y, and dealuminized Y), LTL (e.g., zeolite L), IWW (e.g., ITQ-22), VFI (e.g., VPI-5), AEL (e.g., SAPO-11), AFI (e.g., ALPO-5), and AFO (SAPO-41), as well as materials such as MCM-68, EMM-1, EMM-2, ITQ-23, ITQ-24, ITQ-25, ITQ-26, ETS-2, ETS-10, SAPO-17, SAPO-34, and SAPO-35. Suitable mesoporous materials include MCM-41, MCM-48, MCM-50, and SBA-15.

Examples of preferred catalysts include molybdenum, tungsten, zinc, rhenium, and compounds and combinations thereof on ZSM-5, silica, or alumina.

The metal component can be dispersed on the inorganic support by any means well known in the art such as co-precipitation, incipient wetness, evaporation, impregnation, spray-drying, sol-gel, ion-exchange, chemical vapor deposition, diffusion, and physical mixing. In addition, the inorganic support can be modified by known methods, such as, for example, steaming, acid washing, caustic washing, and/or treatment with silicon-containing compounds, phosphorus-containing compounds, and/or elements or compounds of Groups 1, 2, 3, and 13 of the Periodic Table of the Elements. Such modifications can be used to alter the surface activity of the support and hinder or enhance access to any internal pore structure of the support.

The dehydrocyclization step can be conducted over a wide range of conditions; including, a temperature of from about 400° C. to about 1200° C., or from about 500° C. to about 975° C., or from about 600° C. to about 950° C., an absolute pressure of from about 1 kPa to about 1000 kPa, or from about 10 to about 500 kPa, or from about 50 kPa to about 200 kPa, and a weight hourly space velocity (WHSV is (weight/time of feed)/(weight of catalyst)) of from about 0.01 to about 1000 $hr^{-1}$, or from about 0.1 to about 500 $hr^{-1}$, or from about 1 to about 20 $hr^{-1}$. Preferably, the dehydrocyclization step is conducted in the absence of $O_2$.

The dehydrocyclization step can be conducted in one or more fixed beds, moving beds, or fluidized bed reactors, with catalyst regeneration being conducted in-situ or ex-situ with air, oxygen, carbon dioxide, carbon monoxide, water, $H_2$, or combinations thereof.

The dehydrocyclization reaction is endothermic and, hence when the reaction is conducted in a plurality of stages, it may be necessary to employ interstage heating to return the feed to the required reaction temperature. The fuel required to provide the interstage heating may be obtained by removing and combusting a sidestream from the dehydrocyclization effluent, after separation of the aromatic components and/or alkylated aromatic components. In addition, when the reaction occurs in the presence of a moving bed of catalyst, a portion or all of the heat may be supplied by withdrawing a portion of the catalyst from the bed, heating the catalyst by, for example, combustion of coke on the catalyst and then returning the heated catalyst to the moving catalyst bed.

The major components of the effluent from the dehydrocyclization step are $H_2$, benzene, naphthalene, carbon monoxide, ethylene, and residual methane. Typically, the effluent contains a concentration of aromatic rings which is at least 5 wt %, or at least 10 wt %, or at least 20 wt %, or preferably at least 30 wt %, greater than the concentration of aromatic rings in the feed.

The benzene and naphthalene may then be recovered from the dehydrocyclization effluent, for example, by solvent extraction followed by fractionation. However, as will be discussed below, at least part of these aromatic components can be submitted to an alkylation step, before or after product recovery, to produce higher value materials, such as xylenes.

After recovery of the aromatic hydrocarbons from the dehydrocyclization effluent, at least part of the hydrogen and unreacted methane in the effluent are reacted with $CO_2$, $H_2O$, and/or $O_2$ to produce synthesis gas (typically referred to herein as syngas).

Syngas Generation

Syngas Generation via Steam Methane Reforming

In the catalytic steam reforming process, hydrocarbon feeds are converted to a mixture of $H_2$, CO, and $CO_2$ by reacting hydrocarbons with steam. This process involves the following reactions:

$$CH_4 + H_2O \leftrightarrow CO + 3H_2 \text{(steam reforming)} \quad \text{(Reaction 6)}$$

$$C_nH_m + nH_2O \leftrightarrow nCO + [n+(m/2)]H_2 \quad \text{(Reaction 7)}$$

$$CO + H_2O \leftrightarrow CO_2 + H_2 \text{(shift reaction)} \quad \text{(Reaction 8)}$$

The process is carried out in the presence of a catalyst. Any conventional reforming type catalyst can be used, but generally the catalyst comprises at least one active metal or metal oxide of Group 6 or Groups 8-10 of the Periodic Table of the Elements. The Periodic Table of the Elements referred to herein is that from *CRC Handbook of Chemistry and Physics*, 82$^{nd}$ Edition, 2001-2002, CRC Press LLC, which is incorporated herein by reference.

In one embodiment, the catalyst contains at least one Group 6 or Group 8-10 metal, or oxide thereof. Specific examples of reforming catalysts that can be used are nickel, nickel oxide, cobalt oxide, chromia, and molybdenum oxide. Optionally, the catalyst is employed with at least one promoter. Examples of promoters include alkali and rare earth promoters. Generally, promoted nickel oxide catalysts are preferred.

The amount of Group 6 or Group 8-10 metal in the catalyst can vary, although generally the catalyst includes from about 3 wt % to about 40 wt %, such as from about 5 wt % to about 25 wt %, of at least one Group 6 or Group 8-10 metal, based on total weight of the catalyst.

The reforming catalyst optionally contains one or more metals to suppress carbon deposition during steam reforming. Such metals are selected from the metals of Group 14 and Group 15 of the Periodic Table of the Elements. Preferred Group 14 and Group 15 metals include germanium, tin, lead, arsenic, antimony, and bismuth. Such metals are typically included in the catalyst in an amount of from about 0.1 wt % to about 30 wt %, based on total weight of the Group 6 and/or Group 8-10 metal in the catalyst.

In a catalyst comprising nickel and/or cobalt there may also be present one or more platinum group metals, which are capable of increasing the activity of the nickel and/or cobalt and of decreasing the tendency for carbon lay-down when reacting steam with hydrocarbons higher than methane. The concentration of such platinum group metal is typically from about 0.0005 to about 0.1% as metal, calculated as the whole catalyst unit. Further, the catalyst can contain a platinum group metal but no non-noble catalytic component. Such a catalyst is more suitable for the hydrocarbon steam reforming reaction than one containing a platinum group metal on a conventional support because a greater fraction of the active metal is accessible to the reacting gas. A typical content of platinum group metal when used alone is from about 0.0005 to about 0.5 wt % as metal, calculated on the whole catalytic unit.

Any conventional reformer can be used in the step of catalytic steam reforming. The use of a tubular reformer is preferred. In one embodiment, the steam reforming catalyst is disposed in a plurality of furnace tubes that are maintained at an elevated temperature by radiant heat transfer and/or by contact with combustion gases. Fuel, such as a portion of the hydrocarbon feed, is burned in the reformer furnace to externally heat the reformer tubes therein. See, for example, Kirk-Othmer, *Encyclopedia of Chemical Technology*, 3rd Ed., 1990, vol. 12, p. 951; and *Ullmann's Encyclopedia of Industrial Chemistry*, 5th Ed., 1989, vol. A-12, p. 186, the relevant portions of each being fully incorporated herein by reference.

In one embodiment, the reformer unit includes tubes which are packed with solid catalyst granules. Conveniently, the solid catalyst granules comprise nickel or other catalytic agents deposited on a suitable inert carrier material. For example, the catalyst can comprise nickel oxide (NiO) supported on alumina, calcium aluminate, calcium oxide on alumina, magnesium aluminate, magnesium oxide on alumina, spinel type magnesium aluminum oxide, or calcium aluminate titanate.

In yet another embodiment, both the hydrocarbon feed stream and the steam are preheated prior to entering the reformer. For example, the hydrocarbon feedstock can be preheated to as high a temperature as is consistent with the avoiding of undesired pyrolysis or other heat deterioration. Since steam reforming is endothermic in nature, and since there are practical limits to the amount of heat that can be added by indirect heating in the reforming zones, preheating of the feed is desired to facilitate the attainment and maintenance of a suitable temperature within the reformer itself. Accordingly, it is desirable to preheat both the hydrocarbon feed and the steam to a temperature of at least 200° C., preferably at least 400° C. The reforming reaction is generally carried out at a temperature of from about 500° C. to about 1,200° C., such as from about 800° C. to about 1,100° C., for example from about 900° C. to about 1,050° C.

Gas hourly space velocity in the reformer should be sufficient for providing the desired CO to $CO_2$ balance in the synthesis gas. Conveniently, the gas hourly space velocity (based on wet feed) is from about 3,000 per hour to about 20,000 per hour, such as from about 4,000 per hour to about 9,000 per hour, and for example from about 5,000 per hour to about 8,000 per hour.

Steam reforming is generally carried out at superatmospheric pressure. The specific operating pressure employed is influenced by the pressure requirements of the subsequent process in which the reformed gas mixture is to be employed. Although any superatmospheric pressure can be used in practicing the present process, pressures of from about 1,000 kPa absolute to about 8,000 kPa absolute are desirable. Conveniently, steam reforming is carried out at a pressure of from about 2,170 kPa absolute to about 5,687 kPa absolute, for example from about 2,515 kPa absolute to about 4,928 kPa absolute.

The ratio of steam to hydrocarbon feed will vary depending on the overall conditions in the reformer. The amount of steam employed is influenced by the requirement of avoiding carbon deposition on the catalyst, and by the acceptable methane content of the effluent at the reforming conditions maintained. On this basis, the mole ratio of steam to hydrocarbon feed in the conventional primary reformer unit is preferably of from about 1.5:1 to about 5:1, such as from about 2:1 to about 4:1.

The hydrogen to carbon oxide ratio of the syngas produced will vary depending on the overall conditions of the reformer, but generally will range from about 1:1 to about 5:1.

Syngas Generation via Carbon Dioxide Reforming or Dry Reforming

Dry reforming is the reaction of carbon dioxide with a hydrocarbon to form carbon monoxide and hydrogen. An example for methane and other hydrocarbons is shown in Reactions 5 and 9, respectively.

$$CH_4 + CO_2 \leftrightarrow 2CO + 2H_2 \text{(dry reforming)} \quad \text{(Reaction 5)}$$

$$C_nH_m + nCO_2 \leftrightarrow (2n)CO + (m/2)H_2 \quad \text{(Reaction 9)}$$

The reaction is carried out in the presence of a catalyst. Any conventional reforming type catalyst can be used. In one embodiment, the catalyst contains at least one Group 6 or Group 8-10 metal, or oxide thereof. Specific examples of reforming catalysts that can be used are nickel, nickel oxide, cobalt oxide, chromia, and molybdenum oxide. Optionally, the catalyst is employed with at least one promoter. Examples of promoters include alkali and rare earth promoters. Generally, promoted nickel oxide catalysts are preferred.

The amount of Group 6 or Group 8-10 metals in the catalyst can vary, but conveniently the catalyst includes from about 3 wt % to about 40 wt %, such as from about 5 wt % to about 25 wt %, of at least one Group 6 or Group 8-10 metal, based on total weight of the catalyst.

The reforming catalyst optionally contains one or more metals to suppress carbon deposition during dry reforming. Such metals are selected from the metals of Group 14 and Group 15 of the Periodic Table of the Elements. Suitable Group 14 and Group 15 metals include germanium, tin, lead, arsenic, antimony, and bismuth. Such metals are generally included in the catalyst in an amount of from about 0.1 wt % to about 30 wt %, based on total weight of the Group 6 and/or Group 8-10 metal in the catalyst.

In a catalyst comprising nickel and/or cobalt there may also be present one or more platinum group metals, which are capable of increasing the activity of the nickel and/or cobalt and of decreasing the tendency to carbon lay-down when reacting steam with hydrocarbons higher than methane. The concentration of such platinum group metal is typically from about 0.0005 to about 0.1% as metal, calculated as the whole catalyst unit. Further, the catalyst can contain a platinum group metal but no non-noble catalytic component. Such a catalyst is more suitable for the dry reforming reaction than one containing a platinum group metal on a conventional support because a greater fraction of the active metal is accessible to the reacting gas. A typical content of platinum group metal when used alone is from about 0.0005 to about 0.5 wt % as metal, calculated on the whole catalytic unit.

Any conventional reformer configuration can be used in the step of catalytic dry reforming. The use of a tubular reformer is preferred. In one embodiment, the dry reforming catalyst is disposed in a plurality of furnace tubes that are maintained at an elevated temperature by radiant heat transfer and/or by contact with combustion gases. Fuel, such as a portion of the hydrocarbon feed, is burned in the reformer furnace to externally heat the reformer tubes therein. See, for example, Kirk-Othmer, *Encyclopedia of Chemical Technology*, 3rd Ed., 1990, vol. 12, p. 951; and *Ullmann's Encyclopedia of Industrial Chemistry*, 5th Ed., 1989, vol. A-12, p. 186, the relevant portions of each being fully incorporated herein by reference.

In one embodiment, the reformer unit includes tubes which are packed with solid catalyst granules. Conveniently, the solid catalyst granules comprise nickel or other catalytic agents deposited on a suitable inert carrier material. For example, the catalyst may be NiO supported on alumina, calcium aluminate, calcium oxide on alumina, magnesium aluminate, magnesium oxide on alumina, spinel type magnesium aluminum oxide, or calcium aluminate titanate.

In another embodiment, both the hydrocarbon feed stream and the carbon dioxide are preheated prior to entering the reformer. The hydrocarbon feedstock is conveniently preheated to as high a temperature as is consistent with the avoiding of undesired pyrolysis or other heat deterioration. Since dry reforming is endothermic in nature, and since there are practical limits to the amount of heat that can be added by indirect heating in the reforming zones, preheating of the feed is desired to facilitate the attainment and maintenance of a suitable temperature within the reformer itself. Accordingly, it is desirable to preheat both the hydrocarbon feed and the steam to a temperature of at least 200° C., such as at least 400° C. The reforming reaction is generally carried out at a temperature of from about 500° C. to about 1,200° C., such as from about 800° C. to about 1,100° C.

Gas hourly space velocity in the reformer should be sufficient for providing the desired CO to $CO_2$ balance in the synthesis gas. Conveniently, the gas hourly space velocity (based on (volume/time of wet feed)/(volume of catalyst)) is from about 3,000 per hour to about 10,000 per hour, for example from about 4,000 per hour to about 9,000 per hour, such as from about 5,000 per hour to about 8,000 per hour.

Dry reforming is generally carried out at superatmospheric pressure. The specific operating pressure employed is influenced by the pressure requirements of the subsequent process in which the reformed gas mixture is to be employed. Although any superatmospheric pressure can be used in practicing the process, pressures of from about 1,300 kPa absolute to about 7,700 kPa absolute are desirable. Conveniently, dry reforming is carried out at a pressure of from about 2,170 kPa absolute to about 5,700 kPa absolute, for example from about 2,500 kPa absolute to about 4,930 kPa absolute.

The ratio of carbon dioxide to hydrocarbon feed will vary depending on the overall conditions in the reformer. The amount of carbon dioxide employed is influenced by the requirement of avoiding carbon deposition on the catalyst, and by the acceptable methane content of the effluent at the reforming conditions maintained. The presence of an $H_2$ co-product in the present process is particularly advantageous for use in dry reforming as the $H_2$ will allow use of higher levels of $CO_2$ before coke deposition becomes a significant issue. On this basis, the mole ratio of carbon dioxide to hydrocarbon feed in the primary reformer unit is generally from about 0.75:1 to about 5:1, such as from about 1:1 to about 3:1.

The hydrogen to carbon oxide ratio of the syngas produced will vary depending on the overall conditions of the reformer, but typically will range from about 0.333:1 to about 3:1.

Syngas Generation via Partial Oxidation

This present process further provides for the production of syngas, or CO and $H_2$, by oxidative conversion (also referred to herein as partial oxidation) of hydrocarbon, particularly natural gas. According to the process, hydrocarbon is reacted with free-oxygen to form CO and $H_2$. The process is carried out with or without a catalyst. The use of a catalyst is preferred, preferably with the catalyst containing at least one non-transition or transition metal oxide. The process is essentially exothermic, and is an incomplete combustion reaction, having the following general formula:

$$C_nH_m + (n/2)O_2 \leftrightarrow nCO + (m/2)H_2 \quad \text{(Reaction 10)}$$

Catalytic partial oxidation comprises passing a gaseous hydrocarbon mixture, and oxygen, over reduced or unreduced composite catalysts. The reaction is optionally accompanied by the addition of water vapor (steam) or $CO_2$. When steam or $CO_2$ is added, the reaction is generally referred to as autothermal reduction. An autothermal reduction is both exothermic and endothermic as a result of adding both oxygen and water, or oxygen and carbon dioxide, or oxygen, water and carbon dioxide.

In the partial oxidation process, the catalyst comprises at least one transition element selected from the group consisting of nickel (Ni), cobalt (Co), palladium (Pd), ruthenium (Ru), rhodium (Rh), iridium (Ir), platinum (Pt), osmium (Os), and iron (Fe). Conveniently, the catalyst comprises at least one transition element selected from the group consisting of palladium (Pd), platinum (Pt), and rhodium (Rh). In another embodiment, the catalyst comprises at least one transition element selected form the group consisting of ruthenium (Ru), rhodium (Rh), and iridium (Ir).

In one embodiment, the partial oxidation catalyst further comprises at least one metal selected from the group consisting of titanium (Ti), zirconium (Zr), hafnium (Hf), yitrium (Y), thorium (Th), uranium (U), zinc (Zn), cadmium (Cd), boron (B), aluminum (Al), thallium (Tl), silicon (Si), tin (Sn), lead (Pb), phosphorous (P), antimony (Sb), bismuth (Bi), magnesium (Mg), calcium (Ca), strontium (Sr), barium (Ba), gallium (Ga), vanadium (V), and scandium (Sc). Also, optionally included in the partial oxidation catalyst is at least one rare earth element selected from the group consisting of lanthanum (La), cerium (Ce), praseodymium (Pr), neodymium (Nd), promethium (Pm), samarium (Sm), europium (Eu), gadolinium (Gd), terbium (Tb), dysprosium (Dy), holmium (Ho), erbium (Er), thulium (Tm), ytterbium (Yb), and lutetium (Lu).

In another embodiment the catalyst employed in the process may comprise a wide range of catalytically active components, for example palladium (Pd), platinum (Pt), rhodium (Rh), iridium (Ir), osmium (Os), ruthenium (Ru), nickel (Ni), chromium (Cr), cobalt (Co), cerium (Ce), lanthanum (La), and mixtures thereof. Materials not normally considered to be catalytically active may also be employed as catalysts, for example refractory oxides such as cordierite, mullite, mullite aluminum titanate, zirconia spinels and alumina.

In yet another embodiment, the catalyst is comprised of metals selected from those having atomic numbers 21 to 29, 40 to 47 and 72 to 79: the metals scandium (Sc), titanium (Ti), vanadium (V), chromium (Cr), manganese (Mn), iron (Fe), cobalt (Co), nickel (Ni), copper (Cu), zirconium (Zr), niobium (Nb), molybdenum (Mo), technetium (Tc), ruthenium (Ru), rhodium (Rh), palladium (Pd), silver (Ag), hafnium (Hf), tantalum (Ta), tungsten (W), rhenium (Re), osmium (Os), iridium (Ir), platinum (Pt), and gold (Au). Particularly suitable metals are those from Groups 8-10 of the Periodic Table of the Elements, that is iron (Fe), (osmium (Os), cobalt (Co), rhodium (Rh), iridium (Ir), palladium (Pd), platinum (Pt), nickel (Ni), and ruthenium (Ru).

In another embodiment, the partial oxidation catalyst comprises at least one transition or non-transition metal deposited on a monolith support. The monolith supports can be impregnated with a noble metal such as platinum (Pt), palladium (Pd), or rhodium (Rh), or other transition metals such as nickel (Ni), cobalt (Co), chromium (Cr), and the like. Desirably, these monolith supports are prepared from solid refractory or ceramic materials such as alumina, zirconia, magnesia, ceria, silica, titania, and mixtures thereof. Mixed refractory oxides, that is refractory oxides comprising at least two cations, may also be employed as carrier materials for the catalyst.

In one embodiment, the catalyst is in the form of a fixed arrangement, such as a fixed bed of catalyst particles. Alternatively, the fixed arrangement comprises the catalyst in the form of one or more monolith structures. A suitable monolith structure comprises a ceramic foam.

The catalyst may or may not be reduced before the catalytic reaction. In one embodiment, the catalyst is reduced by passing a gaseous mixture comprising hydrogen and inert gas (e.g., $N_2$, He, or Ar) over the catalyst in a fixed bed reactor at a pressure of from about 100 kPaa to about 500 kpaa, and a temperature of from about 300° C. to about 700° C. Hydrogen gas is typically present in the reduction gas at a concentration of from about 1 mole % to about 100 mole %, based on total amount of reduction gas. Desirably, the reduction is further carried out at a gas hourly space velocity of reducing gas mixture of from about $10^3$ $hr^{-1}$ to about $10^6$ $hr^{-1}$ for a period of from about 0.5 hour to about 20 hours.

In another embodiment, reduction of the partial oxidation catalyst is effected by passing the hydrocarbon feed and oxygen (or air) over the catalyst at temperature of from about 500° C. to about 900° C. for a period of from about 0.1 hour to about 10 hours.

In yet another embodiment, the feed comprises methane, and the feed is injected with oxygen into the partial oxidation reformer at a methane to oxygen (i.e., $O_2$) ratio of from about 1.2:1 to about 10:1, such as from about 1.6:1 to about 8:1, for example from about 1.8:1 to about 4:1.

Water and/or carbon dioxide may or may not be added to the partial oxidation process. When added, the concentration of water and carbon dioxide injected into the reformer is generally not greater than about 65 mole %, based on the total feed content. When water is added to the feed, it is generally added so that the water to methane ratio is not greater than 3:1, preferably not greater than 2:1. When carbon dioxide is added to the feed, it is generally added so that the carbon dioxide to methane ratio is not greater than 2:1.

When water is added to the feed, the $H_2$:CO mole ratio in the product is increased by the shift reaction: $CO + H_2O \leftrightarrow H_2 + CO_2$ (Reaction 8). This reaction occurs simultaneously with the oxidative conversion of the hydrocarbon in the feed to CO and $H_2$ or syngas. The hydrocarbon used as feed in the partial oxidation process is preferably in the gaseous phase when contacting the catalyst. The partial oxidation process is particularly suitable for the partial oxidation of methane, natural gas, associated gas, or other sources of light hydrocarbons. In this respect, the term "light hydrocarbons" is a reference to hydrocarbons having from 1 to 5 carbon atoms. The process may be advantageously applied in the conversion of gas from naturally occurring reserves of methane which contain substantial amounts of carbon dioxide.

In the partial oxidation process, carbon monoxide (CO) and hydrogen ($H_2$) are formed as major products, and water and carbon dioxide ($CO_2$) as minor products. The gaseous product stream comprises the above mentioned products, unconverted reactants (i.e., methane or natural gas, and oxygen) and components of feed other than reactants.

The partial oxidation process is operable over a wide range of pressures. For applications on a commercial scale, elevated pressures, that is pressures significantly above atmospheric pressure, are preferred. In one embodiment, the partial oxidation process is operated at pressures of greater than atmospheric up to about 15,000 kPaa, such as from about 200 kpaa to about 12,500 kPaa, for example from about 500 kpaa to about 10,000 kpaa.

The partial oxidation process is also operable over a wide range of temperatures. At commercial scale, the feed is preferably contacted with the catalyst at high temperatures. In one embodiment, the feed mixture is contacted with the catalyst at a temperature of at least 600° C., such as from about 600° C. to about 1,700° C., for example from about 800° C. to about 1,600° C. The feed mixture is typically preheated prior to contacting the catalyst.

The feed is provided during the operation of the process at a suitable space velocity to form a substantial amount of CO in the product and provide the desired CO to $CO_2$ balance in the syngas. Conveniently, the gas hourly space velocity (based on wet feed) is from about 1,000 per hour to about 100,000 per hour, such as from about 2,000 per hour to about 20,000 per hour.

Syngas Generation via Combination Process

Combination reforming processes can also be used in the present process. Examples of combination reforming processes include autothermal reforming and fixed bed syngas generation. These processes involve a combination of gas phase partial oxidation and steam reforming chemistry.

The autothermal reforming process preferably comprises two syngas generating processes, a primary oxidation process and a secondary steam or dry reforming process. In one embodiment, a hydrocarbon feed stream is steam or dry reformed in a tubular primary reformer by contacting the hydrocarbon and steam and/or $CO_2$ with a reforming catalyst to form a primary reformed gas containing hydrogen and carbon monoxide. The carbon monoxide content of the primary reformed gas is then further increased in the secondary reformer. In one embodiment, the secondary reformer includes a cylindrical refractory lined vessel with a gas mixer, such as in the form of a burner in the inlet portion of the vessel and a bed of nickel catalyst in the lower portion. Conveniently, the exit gas from the primary reformer is mixed with air and residual hydrocarbons, and the mixed gas is partially oxidized to carbon monoxides.

For large-scale production of syngas, the autothermal reformer ("ATR") offers the lowest investment cost. The reforming reactions ($CH_4+H_2O$ or $CH_4+CO_2$ to syngas) are endothermic, and heat must be supplied. In conventional steam reforming or dry reforming, tubular reactors with fired heat on the outside are used. In ATR, oxygen is added to the reactor to generate heat from exothermic oxidation reactions. In the ATR of methane, the amount of oxygen needed to achieve autothermal operation is about 0.52 $O_2$ per $CH_4$ molecule. The stoichiometry of the syngas produced from this ATR is suitable for Fischer Tropsch chemistry, but is substoichiometric in hydrogen for methanol production. For methanol production from ATR syngas, expensive hydrogen recovery and recycle equipment is required in the methanol synthesis loop. In the ATR of a feed containing a methane/$CO_2$ mixture, the stoichiometry of the syngas for methanol is even worse.

The addition of hydrogen to the methane feed to an ATR can provide the correct stoichiometry for methanol, without the need for an expensive hydrogen recovery equipment. There is an additional benefit of having $H_2$ in the feed, in that the temperature in the ATR reactor is reduced for a given methane conversion. The use of an $H_2$ co-feed to the ATR also allows the use of $CO_2$-containing feeds. The presence of a dehydrocyclization reaction step provides this hydrogen in a cost-effective manner.

In another embodiment incorporating the autothermal reforming process, partial oxidation is carried out as the primary oxidizing process. Conveniently, hydrocarbon feed, oxygen, and optionally steam, are heated and mixed at an outlet of a single large coaxial burner or injector which discharges into a gas phase partial oxidation zone. Oxygen is generally supplied in an amount which is less than the amount required for complete combustion.

Upon reaction in the partial oxidation combustion zone, the gases flow from the primary reforming process into the secondary reforming process. In one embodiment, the gases are passed over a bed of steam reforming catalyst particles or a monolithic body, to complete steam reforming. Desirably, the entire hydrocarbon conversion is completed in a single reactor aided by internal combustion.

In an alternative embodiment of this disclosure, a fixed bed syngas generation process is used to form syngas. In the fixed bed syngas generation process, hydrocarbon feed and oxygen or an oxygen-containing gas are introduced separately into a fixed catalyst bed. Preferably, the catalyst is comprised of nickel and supported primarily on alpha alumina.

The fixed bed syngas generation process is carried out at conditions of elevated temperature and pressure that favor the formation of hydrogen and carbon monoxide when, for example, methane is reacted with oxygen and steam. Generally, temperatures are in excess of about 927° C., but not so high as to cause disintegration of the catalyst or the sticking of catalyst particles together. Suitable temperatures range from about 954° C. to about 1,066° C., such as from about 982° C. to about 1,010° C.

Pressure in the fixed bed syngas generation process may range from atmospheric to about 4000 kpaa. In one embodiment, pressures of from about 2,000 kPaa to about 3,000 kPaa are employed, which allows subsequent processes to proceed without intermediate compression of product gases.

In one embodiment, methane, steam, and oxygen are introduced into a fluid bed by separately injecting the components into the bed. Alternatively, each stream is diluted with steam as it enters the bed. For example, methane and steam can be mixed at a methane to steam molar ratio of from about 1:1 to about 3:1, such as from about 1.5:1 to about 2.5:1, and the methane and steam mixture is injected into the bed. Conveniently, the molar ratio of oxygen to methane is from about 0.2:1 to about 1.0:1, such as from about 0.4:1 to about 0.6:1.

In another embodiment of this disclosure, a fluid bed process is used with a nickel based catalyst supported on alpha alumina. Conveniently, the support is comprised of at least 95 wt % alpha alumina, such as at least 98 wt % alpha alumina, based on total weight of the support. In another embodiment, silica is included in the support.

The syngas generated by the present process can be used to produce a variety of valuable products including, by way of non-limiting example, methanol, higher alcohols, acetic acid, ammonia, acetone, acetaldehyde, ethylene oxide, ethylene glycol, dimethyl ether, gasoline, and Fischer Tropsch Liquids.

Hydrogen Rejection

After recovery of the aromatic products and syngas generation, the dehydrocyclization effluent may be subjected to a separation step to generate a methane rich stream for recycle to the dehydrocyclization reactor. If the separation step results in a methane stream containing residual $H_2$, a $H_2$ rejection step is conveniently effected to reduce the $H_2$ content of the effluent before the residual methane is recycled to the dehydrocyclization step to maximize feed utilization. Typically the $H_2$ rejection step comprises reacting at least part of the $H_2$ in the dehydrocyclization effluent with an oxygen-containing species, preferably CO and/or $CO_2$, to produce water and a second effluent having a reduced $H_2$ content as compared with the first (dehydrocyclization) effluent.

Conveniently, the $H_2$ rejection step includes (i) methanation and/or ethanation, (ii) a Fischer-Tropsch process, (iii) synthesis of $C_1$ to $C_3$ alcohols, particularly methanol, and other oxygenates, (iv) synthesis of light olefins, paraffins, and/or aromatics by way of a methanol or dimethyl ether intermediate, and/or (v) selective $H_2$ combustion. These steps may be employed sequentially to gain the greatest benefit; for example Fischer-Tropsch may first be employed to yield a $C_2$-plus enriched stream followed by methanation to achieve high conversion of the $H_2$.

Typically, as described below, the $H_2$ rejection step will generate hydrocarbons, in which case, after separation of the co-produced water, at least portion of the hydrocarbons are conveniently recycled to the dehydrocyclization step. For example, when the hydrocarbons produced in the $H_2$ rejection step comprise paraffins and olefins, the portion recycled to the dehydrocyclization step preferably comprises, paraffins or olefins with 6 or less carbon atoms, or 5 or less carbon atoms, or 4 or less carbon atoms, or 3 or less carbon atoms. When the hydrocarbons produced in the $H_2$ rejection step comprise aromatics, the portion recycled to the dehydrocyclization step preferably comprises single ring aromatic species.

Methanation/Ethanation

In one embodiment the $H_2$ rejection step comprises reaction of at least part of said $H_2$ in said dehydrocyclization effluent with carbon dioxide to produce methane and/or ethane according to the following net reactions:

$$CO_2 + 4H_2 \leftrightarrow CH_4 + 2H_2O \quad \text{(Reaction 11)}$$

$$2CO_2 + 7H_2 \leftrightarrow C_2H_6 + 4H_2O \quad \text{(Reaction 12)}$$

The carbon dioxide employed is preferably part of a natural gas stream and more preferably the same natural gas stream used as the feed to the dehydrocyclization step. When the carbon dioxide is part of a methane-containing stream, the $CO_2:CH_4$ of the stream is preferably maintained between 1:1 and 0.1:1. Mixing of said carbon dioxide-containing stream and said dehydrocyclization effluent is preferably achieved by supplying the gaseous feeds to the inlet of a jet ejector.

The $H_2$ rejection step to produce methane or ethane normally employs a $H_2:CO_2$ molar ratio close to the stoichiometric proportions required for the desired Reaction 11 or Reaction 12, although small variations can be made in the stoichiometric ratio if it is desired to produce a $CO_2$-containing or $H_2$-containing second effluent. The $H_2$ rejection step to produce methane or ethane is preferably effected in the presence of a bifunctional catalyst comprising a metal component, particularly a transition metal or compound thereof, on an inorganic support. Suitable metal components comprise copper, iron, vanadium, chromium, zinc, gallium, nickel, cobalt, molybdenum, ruthenium, rhodium, palladium, silver, rhenium, tungsten, iridium, platinum, gold, gallium, and combinations and compounds thereof. The inorganic support may be an amorphous material, such as silica, alumina or silica-alumina, or like those listed for the dehydroaromatization catalyst. In addition, the inorganic support may be a crystalline material, such as a microporous or mesoporous crystalline material. Suitable porous crystalline materials include the aluminosilicates, aluminophosphates, and silicoaluminophosphates listed above for the dehydrocyclization catalyst.

The $H_2$ rejection step to produce methane and/or ethane can be conducted over a wide range of conditions including a temperature of from about 100° C. to about 900° C., such as from 150° C. to 500° C., for example from 200° C. to 400° C., a pressure of from about 200 kPaa to about 20,000 kPaa, such as from 500 to 5000 kpaa and a weight hourly space velocity of from 0.1 to 10,000 hr$^{-1}$, such as from 1 to 1,000 hr$^{-1}$. $CO_2$ conversion levels are typically between 20 and 100%, preferably greater than 90%, more preferably greater than 99%. This exothermic reaction may be carried out in multiple catalyst beds with heat removal between beds. In addition, the lead bed(s) may be operated at higher temperatures to maximize kinetic rates and the tail beds(s) may be operated at lower temperatures to maximize thermodynamic conversion.

The main products of the reaction are water and, depending on the $H_2:CO_2$ molar ratio, methane, ethane and higher alkanes, together with some unsaturated $C_2$ and higher hydrocarbons. In addition, some partial hydrogenation of the carbon dioxide to carbon monoxide is preferred. After removal of the water, the methane, carbon monoxide, any unreacted carbon dioxide and higher hydrocarbons can be fed directly to the dehydrocyclization step to generate additional aromatic products.

Fischer-Tropsch Process

In another embodiment the $H_2$ rejection step comprises reaction of at least part of said $H_2$ in said dehydrocyclization effluent with carbon monoxide according to the Fischer-Tropsch process to produce $C_2$-$C_5$ paraffins and olefins.

The Fischer-Tropsch process is well known in the art, see for example, U.S. Pat. Nos. 5,348,982 and 5,545,674 incorporated herein by reference. The process typically involves the reaction of $H_2$ and carbon monoxide in a molar ratio of from 0.5:1 to 4:1, preferably 1.5:1 to 2.5:1, at a temperature of from 175° C. to 400° C., preferably from 180° C. to 240° C., and a pressure of from 100 to 10,000 kpaa, preferably from 1,000 to 4,000 kpaa, in the presence of a Fischer-Tropsch catalyst, generally a supported or unsupported Group 8-10, non-noble metal, e.g., Fe, Ni, Ru, Co, with or without a promoter, e.g. ruthenium, rhenium, hafnium, zirconium, titanium. Supports, when used, can be refractory metal oxides such as Group 4, i.e., titania, zirconia, or silica, alumina, or silica-alumina. In one embodiment, the catalyst comprises a non-shifting catalyst, e.g., cobalt or ruthenium, preferably cobalt, with rhenium or zirconium as a promoter, preferably cobalt and rhenium supported on silica or titania, preferably titania.

In another embodiment, the hydrocarbon synthesis catalyst comprises a metal, such as Cu, Cu/Zn or Cr/Zn, on the ZSM-5 and the process is operated to generate significant quantities of single-ring aromatic hydrocarbons. An example of such a process is described in *Study of Physical Mixtures of $Cr_2O_3$-ZnO and ZSM-5 Catalysts for the Transformation of Syngas into Liquid Hydrocarbons* by Jose Erena; Ind. Eng. Chem Res. 1998, 37, 1211-1219, incorporated herein by reference.

The Fischer-Tropsch liquids, i.e., $C_5$-plus hydrocarbons, are recovered and light gases, e.g., unreacted $H_2$ and CO, $C_1$ to $C_3$ or $C_4$, and water are separated from the heavier hydrocarbons. The heavier hydrocarbons can then be recovered as products or fed to the dehydrocyclization step to generate additional aromatic products.

The carbon monoxide required for the Fischer-Tropsch reaction can be provided wholly or partly by the carbon monoxide present in or co-fed with the methane-containing feed and generated as a by-product in the dehydrocyclization step. If required, additional carbon monoxide can be generated by feeding carbon dioxide contained, for example, in natural gas, to a shift catalyst whereby carbon monoxide is produced by the reverse water gas shift reaction:

$$CO_2 + H_2 \leftrightarrow CO + H_2O \quad \text{(Reaction 13)}$$

and by the following reaction:

$$CH_4 + H_2O \leftrightarrow CO + 3H_2 \quad \text{(Reaction 6)}$$

Alcohol Synthesis

In a further embodiment the $H_2$ rejection step comprises reaction of at least part of the $H_2$ in the dehydrocyclization effluent with carbon monoxide to produce $C_1$ to $C_3$ alcohols, and particularly methanol. The production of methanol and other oxygenates from syngas is also well-known and is described in, for example, in U.S. Pat. Nos. 6,114,279; 6,054,497; 5,767,039; 5,045,520; 5,254,520; 5,610,202; 4,666,945; 4,455,394; 4,565,803; 5,385,949, the descriptions of which are incorporated herein by reference. Typically, the syngas employed has a molar ratio of hydrogen ($H_2$) to carbon oxides ($CO + CO_2$) of from 0.5:1 to 20:1, preferably of from 2:1 to 10:1, with carbon dioxide optionally being present in an amount of not greater than 50% by weight, based on total weight of the syngas.

The catalyst used in the methanol synthesis process generally includes an oxide of at least one element selected from the group consisting of copper, silver, zinc, boron, magnesium, aluminum, vanadium, chromium, manganese, gallium, palladium, osmium, and zirconium. Preferably, the catalyst is a copper based catalyst, such as in the form of copper oxide, optionally in the presence of an oxide of at least one element selected from silver, zinc, boron, magnesium, aluminum, vanadium, chromium, manganese, gallium, palladium, osmium, and zirconium. More preferably, the catalyst contains copper oxide and an oxide of at least one element selected from zinc, magnesium, aluminum, chromium, and zirconium. In one embodiment, the methanol synthesis catalyst is selected from the group consisting of: copper oxides, zinc oxides and aluminum oxides. More preferably, the catalyst contains oxides of copper and zinc.

The methanol synthesis process can be conducted over a wide range of temperatures and pressures. Suitable temperatures are from 150° C. to 450° C., such as from 175° C. to 350° C., for example from 200° C. to 300° C. Suitable pressures are from 1,500 kPaa to 12,500 kPaa, such as from 2,000 kpaa to 10,000 kPaa, for example 2,500 kPaa to 7,500 kPaa. Gas hourly space velocities vary depending upon the type of process that is used, but generally the gas hourly space velocity of flow of gas through the catalyst bed is from 50 $hr^{-1}$ to 50,000 $hr^{-1}$, such as from 250 $hr^{-1}$ to 25,000 $hr^{-1}$, for example from 500 $hr^{-1}$ to 15,000 $hr^{-1}$. This exothermic reaction may be carried out in either fixed or fluidized beds, including multiple catalyst beds with heat removal between beds. In addition, the lead bed(s) may be operated at higher temperatures to maximize kinetic rates and the tail beds(s) may be operated at lower temperatures to maximize thermodynamic conversion.

The resultant methanol and/or other oxygenates can be sold as a separate product, can be used to alkylate the aromatics generated in the dehydrocyclization step to higher value products, such as xylenes, or can be used as a feedstock for the production of lower olefins, particularly ethylene and propylene. The conversion of methanol to olefins is a well-known process and is, for example, described in U.S. Pat. No. 4,499,327, incorporated herein by reference.

Selective $H_2$ Combustion

In yet another embodiment, the $H_2$ rejection step comprises selective $H_2$ combustion, which is a process in which $H_2$ in a mixed stream is reacted with oxygen to form water or steam without substantially reacting hydrocarbons in the stream with oxygen to form carbon monoxide, carbon dioxide, and/ or oxygenated hydrocarbons. Generally, selective $H_2$ combustion is carried out in the presence of an oxygen-containing solid material, such as a mixed metal oxide, that will release a portion of the bound oxygen to the $H_2$.

One suitable selective $H_2$ combustion process is described in U.S. Pat. No. 5,430,210, incorporated herein by reference, and comprises contacting at reactive conditions a first stream comprising hydrocarbon and $H_2$ and a second stream comprising oxygen with separate surfaces of a membrane impervious to non-oxygen containing gases, wherein said membrane comprises a metal oxide selective for $H_2$ combustion, and recovering selective $H_2$ combustion product. The metal oxide is typically a mixed metal oxide of bismuth, indium, antimony, thallium, and/or zinc.

U.S. Pat. No. 5,527,979, incorporated herein by reference, describes a process for the net catalytic oxidative dehydrogenation of alkanes to produce alkenes. The process involves simultaneous equilibrium dehydrogenation of alkanes to alkenes and the selective combustion of the $H_2$ formed to drive the equilibrium dehydrogenation reaction further to the product alkenes. In particular, the alkane feed is dehydrogenated over an equilibrium dehydrogenation catalyst in a first reactor, and the effluent from the first reactor, along with oxygen, is then passed into a second reactor containing a metal oxide catalyst which serves to selectively catalyze the combustion of $H_2$. The equilibrium dehydrogenation catalyst may comprise platinum and the selective metal oxide combustion catalyst may contain bismuth, antimony, indium, zinc, thallium, lead, and tellurium or a mixture thereof.

U.S. Patent Application Publication No. 2004/0152586, published Aug. 5, 2004 and incorporated herein by reference, describes a process for reducing the $H_2$ content of the effluent from a cracking reactor. The process employs a catalyst system comprising (1) at least one solid acid cracking component and (2) at least one metal-based selective $H_2$ combustion component consisting essentially of (a) a metal combination selected from the group consisting of:

i) at least one metal from Group 3 and at least one metal from Groups 4-15 of the Periodic Table of the Elements;

ii) at least one metal from Groups 5-15 of the Periodic Table of the Elements, and at least one metal from at least one of Groups 1, 2, and 4 of the Periodic Table of the Elements;

iii) at least one metal from Groups 1-2, at least one metal from Group 3, and at least one metal from Groups 4-15 of the Periodic Table of the Elements; and iv) two or more metals from Groups 4-15 of the Periodic Table of the Elements and (b) at least one of oxygen and sulfur, wherein the at least one of oxygen and sulfur is chemically bound both within and between the metals.

The selective $H_2$ combustion reaction of the present disclosure is generally conducted at a temperature of from 300° C. to 850° C. and a pressure of from 100 to 2000 kPaa.

Aromatic Product Recovery/Treatment

The major products of the dehydrocyclization step are benzene and naphthalene. These products can be separated from the dehydrocyclization effluent, typically by solvent extraction followed by fractionation, and then sold directly as commodity chemicals. Alternatively, some or all of the benzene and/or naphthalene can be alkylated to produce, for example, toluene, xylenes and alkyl naphthalenes and/or can be subjected to hydrogenation to produce, for example, cyclohexane, cyclohexene, dihydronaphthalene (benzylcyclohexene), tetrahydronaphthalene (tetralin), hexahydronaphthalene (dicyclohexene), octahydronaphthalene, and/or decahydronaphthalene (decalin).

Aromatics Alkylation

Alkylation of aromatic compounds such as benzene and naphthalene is well known in the art and typically involves reaction of an olefin, alcohol or alkyl halide with the aromatic species in the gas or liquid phase in the presence of an acid catalyst. Suitable acid catalysts include medium pore zeolites (i.e., those having a Constraint Index of 2-12 as defined in U.S. Pat. No. 4,016,218), including materials having the framework types MFI (e.g., ZSM-5 and silicalite), MEL (e.g., ZSM-11), MTW (e.g., ZSM-12), TON (e.g., ZSM-22), MTT (e.g., ZSM-23), MFS (e.g., ZSM-57) and FER (e.g., ZSM-35) and ZSM-48, as well as large pore zeolites (i.e., those having a Constraint Index of less than 2) such as materials having the framework types BEA (e.g., zeolite beta), FAU (e.g., ZSM-3, ZSM-20, zeolites X, Y, ultrastabilized Y and dealuminized Y), MOR (e.g., mordenite), MAZ (e.g., ZSM-4), MEI (e.g., ZSM-18) and MWW (e.g., MCM-22, PSH-3, SSZ-25, ERB-1, ITQ-1, ITQ-2, MCM-36, MCM-49 and MCM-56).

In one embodiment of the present process, benzene is recovered from the dehydrocyclization effluent and then alkylated with an olefin, such as ethylene produced as a by-product of a $H_2$ rejection step employing ethanation/methanation. Typical conditions for carrying out the vapor phase alkylation of benzene with ethylene include a temperature of from 343 to 482° C., a pressure of from 100 to 20,800 kPaa, a WHSV based on ethylene of from 0.5 to 2.0 $hr^{-1}$ and a mole ratio of benzene to ethylene of from 1:1 to 30:1. Liquid phase alkylation of benzene with ethylene may be carried out at a temperature between 150 to 340° C., a pressure up to about 20,800 kPaa, a WHSV based on ethylene of from 0.1 to 20 $hr^{-1}$ and a mole ratio of benzene to ethylene of from 1:1 to 30:1.

Preferably, the benzene ethylation is conducted under at least partial liquid phase conditions using a catalyst comprising at least one of zeolite beta, zeolite Y, MCM-22, PSH-3, SSZ-25, ERB-1, ITQ-1, ITQ-2, ITQ-13, ZSM-5 MCM-36, MCM-49, and MCM-56.

The benzene ethylation can be conducted at the site of the dehydrocyclization/hydrogen rejection process or the benzene can be shipped to another location for conversion to ethylbenzene. The resultant ethylbenzene can then be sold, used as a precursor in, for example, the production of styrene or isomerized by methods well known in the art to mixed xylenes.

In another embodiment of the present process, the alkylating agent is methanol or dimethylether ("DME") and is used to alkylate benzene and/or naphthalene recovered from the dehydrocyclization effluent to produce toluene, xylenes, methylnaphthalenes, and/or dimethylnaphthalenes. When the methanol or DME is used to alkylate benzene, this is conveniently effected in presence of catalyst comprising a zeolite, such as ZSM-5, zeolite beta, ITQ-13, MCM-22, MCM-49, ZSM-11, ZSM-12, ZSM-22, ZSM-23, ZSM-35, and ZSM-48, which has been modified by steaming so as to have a Diffusion Parameter for 2,2-dimethylbutane of about 0.1-15 $sec^{-1}$ when measured at a temperature of 120° C. and a 2,2-dimethylbutane pressure of 8 kpaa. Such a process is selective to the production of para-xylene and is described in, for example, U.S. Pat. No. 6,504,272, incorporated herein by reference. When the methanol is used to alkylate naphthalene, this is conveniently effected in the presence of a catalyst comprising ZSM-5, MCM-22, PSH-3, SSZ-25, ERB-1, ITQ-1, ITQ-2, ITQ-13, MCM-36, MCM-49 or MCM-56. Such a process can be used to selectively produce 2,6-dimethylnaphthalene and is described in, for example, U.S. Pat. Nos. 4,795,847 and 5,001,295, incorporated herein by reference.

When methanol or DME is used as an alkylating agent in the process of the disclosure, it can be provided as a separate feed to the process or can at least partly be generated in situ by adding a carbon dioxide-containing feed gas, such as a natural gas stream, to part or all of the effluent from the dehydrocyclization step. In particular, the dehydrocyclization effluent, prior to any separation of the aromatic components, can be fed to a reverse shift reactor and reacted with the carbon dioxide-containing feed under conditions to increase the carbon monoxide content of the effluent by reactions, such as Reactions 5 and 13 above.

In addition, methane and $CO_2$ and/or steam may be fed to a reverse shift reactor to generate syngas which can then be mixed with a portion of the dehydrocyclization effluent to adjust the $H_2/CO/CO_2$ ratios as required for the alkylation step.

Typically, the reverse shift reactor contains a catalyst comprising a transition metal on a support, such as Fe, Ni, Cr, or Zn on alumina, silica or titania, and is operated under conditions including a temperature of from 500° C. to 1200° C., such as from 600° C. to 1000° C., for example from 700° C. to 950° C. and a pressure of from 1 kPaa to 10,000 kpaa, such as from 2,000 kpaa to 10,000 kpaa, for example from 3000 kpaa to 5,000 kPaa. Gas hourly space velocities may vary depending upon the type of process used, but generally the gas hourly space velocity of flow of gas through the catalyst bed is of from 50 $hr^{-1}$ to 50,000 $hr^{-1}$, such as from 250 $hr^{-1}$ to 25,000 $hr^{-1}$, more preferably from 500 $hr^{-1}$ to 10,000 $hr^{-1}$.

The effluent from the reverse shift reactor can then be fed to an alkylation reactor operating under conditions to cause reactions such as the following to occur:

  (Reaction 14)

  (Reaction 15)

  (Reaction 16)

Suitable conditions for such an alkylation reactor would include a temperature of from 100 to 700° C., a pressure of from 100 to 30,000 kPaa, and a WHSV for the aromatic hydrocarbon of from 0.01 to 100 $hr^{-1}$. A suitable catalyst would comprise a molecular sieve having a constraint index of 1 to 12, such as ZSM-5, typically together with one or metals or metal oxides, such as copper, chromium and/or zinc oxide.

Preferably, when the alkylation catalyst includes a molecular sieve, the latter is modified to change its diffusion characteristics such that the predominant xylene isomer produced by Reaction 16 is paraxylene. Suitable means of diffusion modification include steaming and ex-situ or in-situ deposition of silicon compounds, coke, metal oxides, such as MgO, and/or P on the surface or in the pore mouths of the molecular sieve. Also preferred is that an active metal be incorporated into the molecular sieve so as to saturate more highly reactive species, such as olefins, which may be generated as by-products and which could otherwise cause catalyst deactivation.

The effluent from the alkylation reactor could then be fed to a separation section in which the aromatic products would initially be separated from the $H_2$ and other low molecular weight materials, conveniently by solvent extraction. The aromatics products could then be fractionated into a benzene fraction, a toluene fraction, a $C_8$ fraction, and a heavy fraction containing naphthalene and alkylated naphthalenes. The $C_8$ aromatic fraction could then be fed to a crystallization or sorption process to separate the valuable p-xylene component and the remaining mixed xylenes either sold as product or fed to an isomerization loop to generate more p-xylene. The toluene fraction could either be removed as a saleable product, recycled to the alkylation reactor or fed to a toluene disproportionation unit, and preferably a selective toluene disproportionation unit for the preparation of additional p-xylene.

Aromatics Hydrogenation

In addition to or instead of the alkylation step, at least part of the aromatic components in the dehydrocyclization effluent can be hydrogenated to generate useful products such as cyclohexane, cyclohexene, dihydronaphthalene (benzylcyclohexene), tetrahydronaphthalene (tetralin), hexahydronaphthalene (dicyclohexene), octahydronaphthalene, and/or decahydronaphthalene (decalin). These products can be employed as fuels and chemical intermediates and, in the case of tetralin and decalin, can be used as the solvent for extracting the aromatic components from the dehydrocyclization effluent.

The hydrogenation is preferably, but not necessarily, conducted after separation of the aromatic components from the dehydrocyclization effluent and preferably employs part of the $H_2$ generated by the dehydrocyclization reaction. Suitable aromatic hydrogenation processes are well known in the art and typically employ a catalyst comprising Ni, Pd, Pt, Ni/Mo, or sulfided Ni/Mo supported on alumina or silica support. Suitable operating conditions for the hydrogenation process include a temperature of from 150 to 540° C., such as from 260 to 370° C., a pressure of from 445 to 13890 kPaa, or from 790 to 3550 kpaa and a WHSV of from 0.5 to 50 $hr^{-1}$, such as from 2 to 10 $hr^{-1}$.

Partial hydrogenation to leave one or more olefinic carbon-carbon bonds in the product may also be desirable so as to produce materials suitable for polymerization or other downstream chemical conversion. Suitable partial hydrogenation processes are well known in the art and typically employ a catalyst comprising noble metals with ruthenium being preferred supported on metallic oxides, such as $La_2O_3$—ZnO. Homogeneous noble metal catalyst systems can also be used. Examples of partial hydrogenation processes are disclosed in U.S. Pat. Nos. 4,678,861; 4,734,536; 5,457,251; 5,656,761; 5,969,202; and 5,973,218, the entire contents of which are incorporated herein by reference.

An alternative hydrogenation process involves low pressure hydrocracking of the naphthalene component to produce alkylbenzenes over a catalyst such as sulfided Ni/W or sulfided Ni supported on an amorphous aluminosilicate or a zeolite, such as zeolite X, zeolite Y or zeolite beta. Suitable operating conditions for low pressure hydrocracking include a temperature of from 150 to 540° C., such as from 260 to 370° C., a pressure of from 445 to 13890 kpaa, such as from 790 to 3550 kpaa and a WHSV of 0.5 to 50 $hr^{-1}$, such as 2 to 10 $hr^{-1}$.

EXAMPLE 1 (COMPARATIVE)

While there are numerous examples of producing syngas from $CO_2$ and methane, these are generally limited to producing 1:1$H_2$:CO molar ratio due to the stoichiometry of:

$$CO_2 + CH_4 \leftrightarrow 2CO + 2H_2 \qquad \text{(Reaction 5)}$$

Typically a higher ratio syngas is desired; for example, for methanol synthesis a molar ratio of about 2.08$H_2$:CO syngas is desired while for FTL a molar ratio of 1.5 to 2.5$H_2$:CO syngas is desired. To achieve these higher ratios an additional separation step must be normally performed to remove a portion of the CO from the stream to yield syngas with a desirable $H_2$:CO ratio. Therefore, for every 100 kg of methane fed, a co-feed of 275 kg of $CO_2$ is needed, but this can only produce 200 kg of 2:1$H_2$:CO syngas (175 kg CO and 25 kg $H_2$) and a lower value byproduct stream of 175 kg of CO. Note that in this example and the others that follow, the fuel requirements for the process are not included as these are highly dependent on the exact equipment utilized.

EXAMPLE 2 (COMPARATIVE)

Co-feeding steam with methane produces higher ratio syngas, however, these are limited to producing 3:1$H_2$:CO molar ratio due to the stoichiometry of:

$$CH_4 + H_2O \leftrightarrow CO + 3H_2 \qquad \text{(Reaction 6)}$$

To achieve a 2:1$H_2$:CO syngas an additional separation step must be performed to remove a portion of the $H_2$ from the stream to yield syngas with a 2:1$H_2$:CO ratio. Therefore, for every 100 kg of methane fed, a co-feed 112.5 kg of $H_2O$ is required, but this only produces 200 kg of 2:1$H_2$:CO syngas (175 kg CO and 25 kg $H_2$) and a lower value byproduct stream of 12.5 kg of $H_2$.

EXAMPLE 3 (COMPARATIVE)

Co-feeding steam and $CO_2$ with methane can be used to directly produce 2:1$H_2$:CO without additional separation by the net reaction:

$$3CH_4 + CO_2 + 2H_2O \leftrightarrow 8H_2 + 4CO$$

For every 100 kg of methane fed, a co-feed 75 kg of $H_2O$ and 92 kg of $CO_2$ is required to produce 266.67 kg of 2:1$H_2$:CO syngas (233 kg CO and 33 kg $H_2$). However, the $CO_2$ content of the feed stream is now limited to 25 volume % $CO_2$, therefore, higher $CO_2$ containing gas fields can not be utilized without additional processing steps to reduce the $CO_2$ content.

EXAMPLE 4

In a simulated embodiment of the present process, methane and $CO_2$ are combined with a dehydrocyclization reaction effluent comprising $H_2$ and residual methane, after the benzene and naphthalene products have been separated from the effluent, and reacted to produce syngas with high value utility and residual methane which can be recycled back to the dehydrocyclization reactor.

In this example, 280 kg of methane rich stream enters the dehydrocyclization reaction zone as a recycle stream from the syngas generation step described below. The dehydrocyclization step is conducted at a temperature of 800° C., a pressure of 140 kPa absolute (965 kPaa) and a weight hourly space velocity of 1.0 $hr^{-1}$. The dehydrocyclization step is conducted over a fixed bed of 2.7 wt % Mo on 25:1 HZSM-5 catalyst with a normalized net carbon selectivity of 70% benzene, 20% naphthalene, and 10% coke. From the dehydrocyclization reaction zone a 4 kg coke product stream and a gaseous product stream are recovered. The gaseous product stream is then subjected to an absorbent based separation step resulting in an aromatics rich stream containing 32 kg of benzene and 9 kg of naphthalene and a residual methane and $H_2$ rich stream.

The methane and $H_2$ rich stream is then combined with a feed of 100 kg of methane and 121 kg $CO_2$ in a syngas generation zone. Syngas generation occurs at a temperature of about 900° C., a pressure of about 1700 kPa absolute (11720 kPaa) and a gas hourly space velocity of about 6,000 $hr^{-1}$ over a catalyst comprising 20 wt % Ni on magnesium aluminum oxide. The syngas generation results in about a 98% conversion of the $CO_2$, and yields a product comprised of 154 kg CO, 22 kg $H_2$, and 280 kg of residual methane. The residual methane is recycled back to the dehydrocyclization step.

EXAMPLE 5

In a further simulated embodiment of the present process, $CO_2$ and $O_2$ can be combined with a dehydrocyclization reaction effluent comprising $H_2$ and residual methane, after the benzene and naphthalene products have been separated from the effluent, and reacted to produce syngas with high value.

In this example, 100 kg of a methane rich stream enters the dehydrocyclization reaction zone. The dehydrocyclization step is conducted at a temperature of 800° C., a pressure of 140 kPa absolute (965 kPaa) and a weight hourly space velocity of 1.0 $hr^{-1}$. The dehydrocyclization step is conducted over a fixed bed of 4.9 wt % Mo on 25:1 HZSM-5 catalyst with a normalized net carbon selectivity of 91% benzene, 9% naphthalene, and 0% coke (coke is internally recycled within the reactor system in this example). From the dehydrocyclization reaction zone a gaseous product stream is recovered and is then subjected to an absorbent based separation step resulting in an aromatics rich stream containing 15 kg of benzene and 1 kg of naphthalene and a residual methane and $H_2$ rich stream.

The methane and $H_2$ rich stream is then combined with a feed of 41 kg $CO_2$ and 65 kg of $O_2$ in a syngas generation zone. Syngas generation occurs at a temperature of about 900° C., a pressure of about 1700 kPa absolute (11720 kPaa) and a gas hourly space velocity of about 6,000 $hr^{-1}$ over a catalyst comprising 20 wt % Ni on magnesium aluminum oxide. The syngas generation yields a net product comprised of 166 kg CO and 24 kg $H_2$. This example has the advantage of producing a larger ratio of syngas to aromatics and not requiring significant gas separations.

Examples 4 and 5 demonstrate that the present process:
A. Produces high value aromatic and syngas products;
B. Can utilize higher $CO_2$ content feed stream than combined methane, $CO_2$, and steam reforming;
C. Does not produce the large volumes of byproduct $H_2$ or CO as do dry or steam reforming, thereby improving overall efficiency and reducing investment required for separations; and
D. Utilizes less $O_2$ and more $CO_2$ than is required for autothermal reforming of a methane stream not containing $H_2$ thereby reducing the investment and improving energy efficiency.

While the present disclosure has been described and illustrated by reference to particular embodiments, those of ordinary skill in the art will appreciate that the disclosure lends itself to variations not necessarily illustrated herein. For this reason, then, reference should be made solely to the appended claims for purposes of determining the true scope of the present disclosure.

The invention claimed is:

1. A process for converting a feed containing methane to syngas and aromatic hydrocarbon(s), the process comprising:
   (a) contacting a feed containing methane with a dehydrocyclization catalyst under conditions effective to produce a first effluent comprising said aromatic hydrocarbons, residual methane, and $H_2$, wherein said first effluent has a concentration of aromatic rings which is at least 5 wt % greater than the concentration of aromatic rings in said feed;
   (b) recovering at least a portion of said aromatic hydrocarbons from said first effluent; and,
   (c) reacting at least part of said $H_2$ and said residual methane from said first effluent with an oxygen-containing species to produce a second effluent having $H_2$ and CO, wherein the total number of moles of $H_2$ and CO in said second effluent is greater than the total number of moles of $H_2$ and CO in said first effluent.

2. The process of claim 1 wherein said feed in step (a) further comprises at least one of $H_2$, $H_2O$, $O_2$, CO and $CO_2$.

3. The process of claim 1 wherein said feed in step (a) comprises less than 5 wt % of $C_3$+hydrocarbons.

4. The process of claim 1 wherein said conditions in step (a) are non-oxidizing conditions.

5. The process of claim 1 wherein said conditions in step (a) include a temperature of from about 400° C. to about 1200° C., an absolute pressure of from about 1 kPa to about 1000 kPa and a weight hourly space velocity of from about 0.1 $hr^{-1}$ to about 1000 $hr^{-1}$.

6. The process of claim 1 wherein said dehydrocyclization catalyst comprises a metal or compound thereof on an inorganic support.

7. The process of claim 1 wherein said dehydrocyclization catalyst comprises at least one of molybdenum, tungsten, zinc, rhenium, a molybdenum compound, a tungsten compound, a zinc compound, and a rhenium compound on ZSM-5, silica or an aluminum oxide.

8. The process of claim 1 wherein said an oxygen-containing species in (c) comprises steam.

9. The process of claim 8 wherein said reacting (c) is conducted in the presence of a catalyst comprising an element selected from one Group 6 or Groups 8 to 10 of the Periodic Table, or oxide thereof, optionally containing one or more metals selected from Group 14 and Group 15 of the Periodic Table.

10. The process of claim 8 wherein said reacting (c) is conducted under conditions comprising a temperature of from about 500° C. to about 1,200° C., an absolute pressure of from about 1,300 kPa to about 8,000 kPa and a weight hourly space velocity of from about 3,000 per hour to about 10,000 per hour.

11. The process of claim 1 wherein said an oxygen-containing species in (c) comprises carbon dioxide.

12. The process of claim 11 wherein said carbon dioxide is introduced to the process as part of a natural gas stream.

13. The process of claim 12 wherein said natural gas stream further comprises at least part of the methane in the feed in step (a).

14. The process of claim 11 wherein said reacting (c) is conducted in the presence of a catalyst comprising an element selected from one Group 6 or Groups 8 to 10 of the Periodic Table, or oxide thereof, optionally containing one or more metals selected from Group 14 and Group 15 of the Periodic Table.

15. The process of claim 11 wherein said reacting (c) is conducted under conditions comprising a temperature of from about 500° C. to about 1,200° C., an absolute pressure of from about 1,300 kPa to about 7,700 kPa and a weight hourly space velocity of from about 3,000 per hour to about 20,000 per hour.

16. The process of claim 1 wherein said an oxygen-containing species in (c) comprises molecular oxygen.

17. The process of claim 16 wherein said reacting (c) is conducted in the presence of a catalyst comprising at least one element selected from the group consisting of nickel (Ni), cobalt (Co), palladium (Pd), ruthenium (Ru), rhodium (Rh), iridium (kr), platinum (Pt), osmium (Os), and iron (Fe).

18. The process of claim 16 wherein said reacting (c) is conducted under conditions comprising a temperature of from about 600° C. to about 1,700° C., an absolute pressure up to about 15,000 kPa and a weight hourly space velocity of from about 1,000 per hour to about 100,000 per hour.

19. The process of claim 1 wherein part of said first effluent is used as fuel to provide heat to step (a).

20. The process of claim 1 and further comprising alkylating at least part of said aromatic hydrocarbons in said first effluent with an alkylating agent, before or after said recovering (b).

21. The process of claim 1 and further including reacting at least a portion of the recovered aromatic hydrocarbons with $H_2$ from said first or second effluent.

22. The process of claim 1 and further including recovering the $H_2$ and CO from said second effluent.

23. The process of claim 1 wherein the molar ratio of $H_2$ to CO in said second effluent is greater than 1.01.

24. The process of claim 1 wherein the molar ratio of $H_2$ to CO in said second effluent is greater than 1.5.

25. The process of claim 1 wherein the molar ratio of $H_2$ to CO in said second effluent is greater than 2.0.

26. The process of claim 1 and further comprising recovering at least part of said residual methane in said first effluent and recycling it to (a).

27. A process for converting a feed containing methane to syngas and aromatic hydrocarbon(s), the process comprising:
  (a) contacting a feed containing methane with a dehydrocyclization catalyst under conditions effective to produce a first effluent comprising said aromatic hydrocarbons, residual methane, and $H_2$, wherein said first effluent has a concentration of aromatic rings which is at least 5 wt % greater than the concentration of aromatic rings in said feed;
  (b) recovering at least a portion of said aromatic hydrocarbons from said first effluent; and,
  (c) reacting at least part of said $H_2$ and said residual methane from said first effluent with an oxygen-containing species comprising $CO_2$, $H_2O$, and/or $O_2$ to produce a second effluent comprising $H_2$, CO, and methane, wherein the total number of moles of $H_2$ and CO in said second effluent is greater than the total number of moles of $H_2$ and CO in said first effluent.

28. The process of claim 27 wherein said feed in step (a) further comprises at least one of $H_2$, $H_2O$, $O_2$, CO and $CO_2$.

29. The process of claim 27 wherein said conditions in step (a) are non-oxidizing conditions including a temperature of from about 400° C. to about 1200° C., an absolute pressure of from about 1 kPa to about 1000 kPa and a weight hourly space velocity of from about 0.1 $hr^{-1}$ to about 1000 $hr^{-1}$.

30. The process of claim 27 wherein said dehydrocyclization catalyst comprises a metal or compound thereof on an inorganic support.

31. The process of claim 27 wherein said dehydrocyclization catalyst comprises at least one of molybdenum, tungsten, zinc, rhenium, a molybdenum compound, a tungsten compound, a zinc compound, and a rhenium compound on ZSM-5, silica or an aluminum oxide.

32. The process of claim 27 wherein said an oxygen-containing species in (c) comprises steam.

33. The process of claim 32 wherein said reacting (c) is conducted in the presence of a catalyst comprising an element selected from one Group 6 or Groups 8 to 10 of the Periodic Table, or oxide thereof, optionally containing one or more metals selected from Group 14 and Group 15 of the Periodic Table.

34. The process of claim 32 wherein said reacting (c) is conducted under conditions comprising a temperature of from about 500° C. to about 1,200° C., an absolute pressure of from about 1,300 kPa to about 8,000 kPa and a weight hourly space velocity of from about 3,000 per hour to about 10,000 per hour.

35. The process of claim 27 wherein said an oxygen-containing species in (c) comprises carbon dioxide.

36. The process of claim 35 wherein said carbon dioxide is introduced to the process as part of a natural gas stream.

37. The process of claim 36 wherein said natural gas stream further comprises at least part of the methane in the feed in step (a).

38. The process of claim 35 wherein said reacting (c) is conducted in the presence of a catalyst comprising an element selected from one Group 6 or Groups 8 to 10 of the Periodic Table, or oxide thereof, optionally containing one or more metals selected from Group 14 and Group 15 of the Periodic Table.

39. The process of claim 35 wherein said reacting (c) is conducted under conditions comprising a temperature of from about 500° C. to about 1,200° C., an absolute pressure of from about 1,300 kPa to about 7,700 kPa and a weight hourly space velocity of from about 3,000 per hour to about 20,000 per hour.

40. The process of claim 27 wherein said an oxygen-containing species in (c) comprises molecular oxygen.

41. The process of claim 40 wherein said reacting (c) is conducted in the presence of a catalyst comprising at least one element selected from the group consisting of nickel (Ni), cobalt (Co), palladium (Pd), ruthenium (Ru), rhodium (Rh), iridium (Ir), platinum (Pt), osmium (Os), and iron (Fe).

42. The process of claim 40 wherein said reacting (c) is conducted under conditions comprising a temperature of from about 600° C. to about 1,700° C., an absolute pressure up to about 15,000 kPa and a weight hourly space velocity of from about 1,000 per hour to about 100,000 per hour.

43. The process of claim 27 and further comprising alkylating at least part of said aromatic hydrocarbons in said first effluent with an alkylating agent, before or after said recovering (b).

44. The process of claim 27 and further including reacting at least a portion of the recovered aromatic hydrocarbons with $H_2$ from said first or second effluent.

45. The process of claim 27 and further including recovering the $H_2$ and CO from said second effluent.

46. The process of claim 27 wherein the molar ratio of $H_2$ to CO in said second effluent is greater than 1.01.

47. The process of claim 27 wherein the molar ratio of $H_2$ to CO in said second effluent is greater than 1.5.

48. The process of claim 27 wherein the molar ratio of $H_2$ to CO in said second effluent is greater than 2.0.

49. The process of claim 27 and further comprising recovering at least part of said residual methane in said first effluent and recycling it to (a).

50. The process of claim 27 and further comprising recovering at least part of said residual methane in said second effluent and recycling it to (a).

* * * * *